United States Patent [19]
LaHaye et al.

[11] Patent Number: 4,877,781
[45] Date of Patent: Oct. 31, 1989

[54] MEDICAL DISPENSER AND PREPARATION FOR INFLAMED TISSUE

[75] Inventors: Peter G. LaHaye, Medina, Wash.; John A. Selling, Menlo Park, Calif.

[73] Assignee: Peter G. LaHaye, Medina, Wash.

[21] Appl. No.: 102,877

[22] Filed: Sep. 30, 1987

[51] Int. Cl.$^4$ .............................................. A61K 31/56
[52] U.S. Cl. .................................... 514/179; 514/886; 514/887; 514/882
[58] Field of Search ............... 514/179, 827, 873, 882, 514/944, 953, 930, 960

[56] References Cited

U.S. PATENT DOCUMENTS

| | | | |
|---|---|---|---|
| 2,975,099 | 3/1961 | Goyan et al. | 514/179 |
| 2,992,265 | 9/1961 | Duane et al. | 15/506 |
| 3,150,049 | 9/1964 | Emory | 167/90 |
| 3,414,927 | 12/1968 | Worcester | 15/104.93 |
| 3,485,349 | 12/1969 | Chaney Jr. | 206/56 |
| 3,657,760 | 4/1972 | Kudisch | 15/104.93 |
| 4,241,048 | 12/1980 | Durbak et al. | 526/264 |
| 4,305,936 | 12/1981 | Klein | 514/179 |
| 4,331,653 | 5/1982 | Brown et al. | 514/941 |
| 4,383,986 | 5/1983 | Dubash et al. | 424/443 |
| 4,437,567 | 3/1984 | Jeng | 206/210 |
| 4,514,384 | 4/1985 | Gallina | 514/882 |

Primary Examiner—H. M. S. Sneed
Assistant Examiner—James Saba
Attorney, Agent, or Firm—Price, Gess & Ubell

[57] ABSTRACT

A hemorrhoidal treatment compound includes pharmaceutically effective amounts of a hydrocortisone compound, pramoxine hydrogen chloride, and ephedrine sulfate. The compound may further contain witch hazel, glycerin, vitamin A, and propylene glycol. The compound is provided in a disposable application kit that includes an absorbent pad with the improved compound absorbed therein for use as a swab or compress. The absorbent pad is further sealed in a wrapping, all of which may be disposed of after a single use.

20 Claims, 1 Drawing Sheet

MEDICAL DISPENSER AND PREPARATION FOR INFLAMED TISSUE

BACKGROUND OF THE INVENTION

1. Field of the Invention

The present invention relates generally to a compound and method for the treatment of hemorrhoidal tissue and, more specifically, to an improved composition and method for the treatment of hemorrhoidal and other types of inflamed tissue which may be utilized within the context of a disposable application kit.

2. Description of Related Art

Various types of hemorrhoid treatment compounds have been been developed in the past to generally reduce the burning, itching, and edema associated with hemorrhoids. These compounds are disclosed, for example, in U.S. Pat. No. 2,436,673 and U.S. Pat. No. 4,514,384. Competition in the manufacturing industry for hemorrhoid compounds has continued to increase. In the recent past, manufacturers have heavily advertised, particularly through the television media, numerous over-the-counter hemorrhoid treatment compounds for direct purchase by consumers.

Still, consumers continually search for hemorrhoid treatment compounds that are not only safe but also effective and easy to use. Despite the large number of treatment compounds available, consumers still have a need to find a treatment compound that is particularly suited for them. A significant number of consumers receive allergic reactions from treatment compounds which may result, for example, from the specific anesthetic used. Another drawback to past hemorrhoid treatment compounds is that many have been in the form of ointments that are difficult to apply. Also, the industry has not given significant attention to the provision of an astringent type compound that creates a "clean" sensation.

A need still exists in the art to provide an improved hemorrhoid treatment compound that is effective, easy to use, and in the form of a dispensing kit that is disposable after a single use.

SUMMARY OF THE INVENTION

An object of the present invention is to provide an improved inflamed tissue treatment compound and method of treating inflamed tissue.

Another object of the present invention is to provide a hemorrhoid treatment compound that minimizes the incidence of allergic reactions and sensitization to the compound.

A further object of the present invention is to provide an improved hemorrhoid treatment compound that reduces the amount of arterio-venous shunting that occurs with hemorrhoids.

An even further object of the present invention is to provide a hemorrhoid compound that maintains the integrity of the epithelium while preventing over-keratinization.

It is also an object of the present invention to provide a hemorrhoid treatment application kit that is easy to carry and disposable after a single use.

The objects of the present invention are particularly accomplished by applying to the inflamed tissue a composition comprising a hydrocortisone compound in an amount which is less than about 2.0% by volume; pramoxine hydrogen chloride in an amount which is less than about 3.0% by volume; and ephedrine sulfate in an amount which is less than about 1.0% by volume.

These and other objects of the present invention can best be seen from an examination of the specification, claims, and drawings hereto.

DESCRIPTION OF THE PREFERRED EMBODIMENTS

Figure 1:
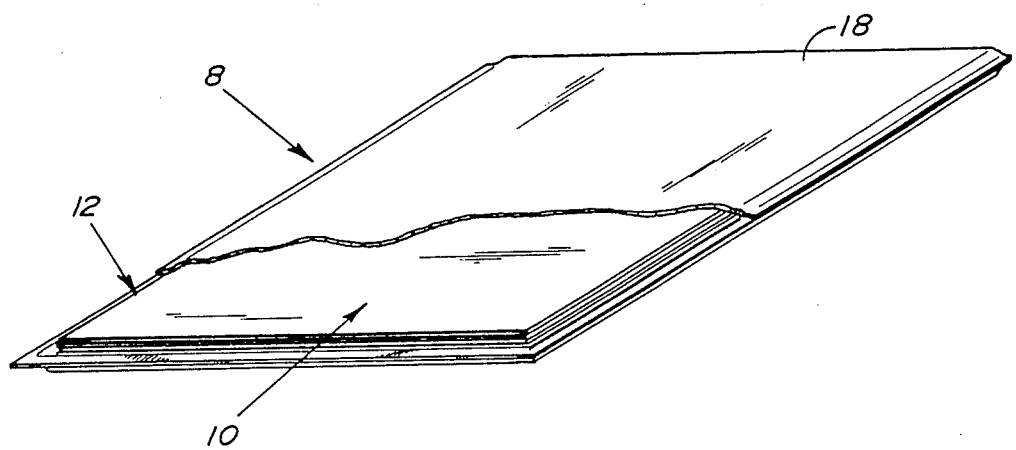
FIG. 1 is a perspective view of an application kit having an absorbent pad with an improved hemorrhoid treatment compound absorbed therein according to the present invention.

The following description is provided to enable a person skilled in the internal medicine and pharmaceutical fields to make and use the present invention and sets forth the best mode contemplated by the inventors of carrying out their invention. Various modifications, however, will remain readily apparent to those skilled in the arts, since the generic principles of the present invention have been defined herein specifically to provide an improved composition for the treatment of inflamed tissues and method of treating same.

While the present invention is disclosed in the context of hemorrhoid treatment, it should be understood that the composition and method of the present invention can also be applied, for example, on perianal fissures, puritis ani, perianal inflammation associated with diarrhea, perianal psoriasis, diaper rash, and contact dermatitis.

The present invention includes an improved inflamed tissue or hemorrhoid treatment composition which includes hydrocortisone acetate, which has the chemical formula $C_{23}H_{32}O_6$ (pregn-4-ene-3, 20-dione, 21-(acetyloxy)-11, 17-dihydroxy-, (11$\beta$)-). The hydrocortisone acetate is a topical corticosteroid that reduces itching, burning, and edema by virtue of its anti-inflammatory, anti-pruritic and vasoconstrictive actions.

The hydrocortisone acetate is preferably used in an amount which is not more than about 2.0% by volume and not less than about 0.25% by volume. More preferably, the hydrocortisone is not more than about 1.0% and not less than about 0.5% by volume. The present invention contemplates using other types of hydrocortisone. In general, however, the acetate derivative is very suitable for topical use since it is insoluble in water and thus less readily absorbed after application than other hydrocortisone derivatives. The present invention also contemplates using tixocortol pivolate (pregn-4-ene-3, 20-dione-21-thiol-11$\beta$, 17-dihydroxy-21-pivolate). This hydrocortisone derivative is not perceptibly absorbed topically and is ideal as the systemic side effects of hydrocortisone are greatly reduced.

The present composition further includes pramoxine hydrogen chloride having the chemical formula $C_{17}H_{27}NO_3 \cdot HCl$ (morpholine, 4-[3-(4-butoxyphenoxy)propyl]-, hydrochloride). The pramoxine hydrogen chloride is a rapidly acting local anesthetic for skin and mucous membrane. Pramoxine hydrogen chloride is preferably used over other anesthetics such as procaine, cocaine, lidocaine, and dibucaine. These latter anesthetics have shown an allergy incidence rate of 10% to 20%. The pramoxine hydrogen chloride is preferably used in that it may often be successfully used on patients previously sensitized to other surface anesthetics. Moreover, the pramoxine hydrogen chloride can be used without significant sensitization to the patient and is substantially free of toxicity.

Preferably, the pramoxine hydrogen chloride is used in an amount which is less than about 3.0% by volume. More preferably, it is used in an amount which is not less than about 0.5% and not more than about 2.0% by volume.

Ephedrine sulfate, having the chemical formula $(C_{10}H_{15}NO)_2 \cdot H_2SO_4$, is also added to the compound to provide vasoconstrictive benefits. The vasoconstrictive effects are accomplished by the ability of ephedrine sulfate to minimize arterio-venous shunting, i.e., arterial flow and resultant high arterial pressures in hemorrhoidal veins. The ephedrine sulfate promotes weak vascular alpha-agonist activity, rather than strong alpha-agonist activity that leads to tissue ischemia which would be counterproductive. The ephedrine sulfate may be provided in an amount which is less than about 1.0% by volume. Preferably, the ephedrine sulfate may be present in amount which is not greater than about 0.3% and not less than about 0.1% by volume.

Witch hazel may also be added to the present compound to provide additional constrictive properties useful in mild bleeding. The witch hazel is an astringent that creates a local constrictive sensation and provides a "clean" or "tingly" feeling. Witch hazel is prepared by macerating recently cut and partially dried dormant twigs of Hamamelis Virginiana L. in water, distilling, and adding alcohol to the distillate, as is well known in the art and described in the THE PHARMACEUTICAL CODEX, page 406, 11th Ed., 1979. Hamamelis contains tannins, principally β-Hamamelitannin, the digalloyl ester of Hamamelose (2 hydroxymethyl ribose), gallic acid, a bitter principle, and a trace of volatile oil. Preferably, the witch hazel is present in an amount between about 30% and about 60% by volume.

Glycerine, having the chemical formula $C_3H_8O_3$, is added to the compound and acts as an emollient, humectant, lubricant, and vehicle. The glycerine, which is substantially non-allergenic, is preferably added in an amount between about 5% and about 15% by volume.

Vitamin A, such as that found in shark or fish liver oil, may also be added to the present composition to maintain the integrity of the epithelium and prevent over-keratinization. The Vitamin A also assists in decreasing mild inflammation of the hemorrhoidal tissue. Additionally, the Vitamin A provides emollient effects. The Vitamin A may be added in an amount between about 1% and about 5% by volume.

Propylene glycol ($C_3H_8O_2$) may also be added in an amount of not less than about 20% nor more than about 40% by volume. The propylene glycol provides a cream or lotion type consistency, as opposed to an ointment.

The composition may further include an anti-bacterial and/or anti-fungal agent. Preferably, the trade-named compound methylparaben is added in an amount of about 0.5% by volume, and more preferably not less than about 0.25% nor more than about 1.0% by volume.

Citric acid ($C_6H_8O_7$) or acetic acid ($C_2H_4O_2$) is preferably added to the composition to buffer the composition at a slightly acidic pH of about 6.0 to 7.0. The buffered compound is thereby compatible, insofar as pH, with the human body.

An emulsifier, such as lectithin, may also be used in an amount between about 0.1% and about 5% by volume.

Examples of preferred embodiments of the present invention are found in the following formulations wherein percentages are by volume:

EXAMPLE 1

| Example 1 | |
|---|---|
| Hydrocortisone acetate | 1% |
| Pramoxine hydrogen chloride | 1% |
| Ephedrine sulfate | 0.2% |
| Witch hazel (aqueous) | 50% |
| Glycerine | 10% |
| Vitamin A | 3% |
| Propylene glycol | 34.3% |
| Methylparaben | 0.5% |

EXAMPLE 2

| Example 2 | |
|---|---|
| Tixocortol pivolate | 1% |
| Pramoxine hydrogen chloride | 1% |
| Ephedrine sulfate | 0.2% |
| Witch hazel (aqueous) | 50% |
| Glycerine | 10% |
| Vitamin A | 3% |
| Propylene glycol | 34.3% |
| Methylparaben | 0.5% |

Figure 2:
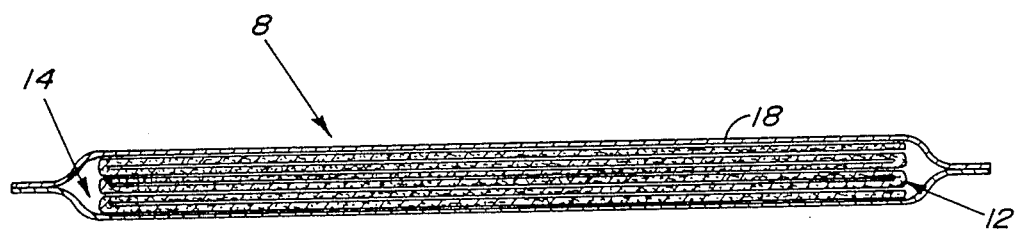
FIG. 2 is an enlarged, cross-sectional view of the application kit with absorbent pad taken across line 2—2 of FIG. 1.
Figure 3:
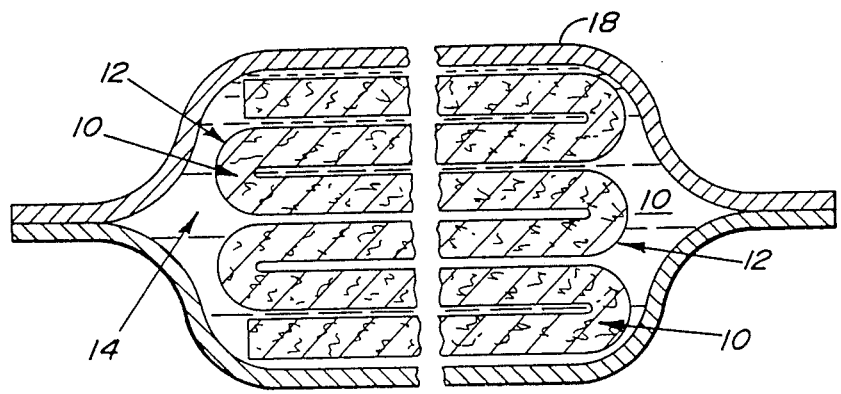
FIG. 3 is a partial, cross-sectional view of an absorbent pad which is kept moist in an application kit.

The present compound 10 can be used in the form of a single use application kit 8 (FIG. 1). For such a use, the compound 10 is absorbed in an absorbent pad or material 12 preferably made of a paper cloth material (FIG. 3). The pad 12 is preferably folded to provide a more compact-sized application kit 8. As shown in FIGS. 1 and 2, the pad 12 having the present compound 10 absorbed therein is enclosed within a sealed environment 14 provided by the kit 8. The sealed environment 14 provides an environment which keeps the pad 12 moist with the compound 10 therein. The kit 8 includes an outer wrapping 18, such as that disclosed in U.S. Pat. No. 2,999,265.

The provision of the kit 8 with the absorbent pad 12 enables a user to easily carry the treatment compound and allows for ready application and easy disposal after a single use. Moreover, the absorbent pad 12 may be used as a swab or as a compress.

The specifications above describe only the preferred embodiments of the present invention, and it is contemplated that various modifications to the above can be effected but nevertheless come within the scope of the present invention as defined by the claims.

What is claimed is:

1. A composition for the treatment of inflamed tissue, comprising:
   tixocortol pivolate in an amount sufficient to provide anti-inflammatory, anti-pruritic, and vasoconstrictive effects to the inflamed tissue;
   pramoxine hydrogen chloride in an amount sufficient to anesthetize the inflamed tissue; and
   ephedrine sulfate in an amount sufficient to minimize arterio-venous shunting of the inflamed tissue.

2. The composition of claim 1 further including witch hazel.

3. The composition of claim 1 further including an emollient agent.

4. The composition of claim 1 further including a buffering agent to maintain a slightly acidic pH of the composition.

5. The composition of claim 1 further including an agent for maintaining the integrity of epithelium tissue and preventing over-keratinization of the inflamed tissue.

6. The composition of claim 1 further including an agent to minimize bacterial and fungal growth.

7. The composition of claim 1 further including an emulsifying agent.

8. The composition of claim 1 further including propylene glycol.

9. A method of treating hemorrhoidal tissue, comprising the steps of:
   applying to the hemorrhoidal tissue of mammals, including humans, a composition comprising:
   a hydrocortisone composition in an amount between about 0.2% and 2.0% by volume, the compound being selected from the group consisting of hydrocortisone acetate and tixocortol pivolate;
   pramoxine hydrogen chloride in an amount between about 0.5% and 3.0% by volume;
   ephedrine sulfate in an amount between about 0.1% and 1.0% by volume;
   witch hazel in an amount between about 30% and 60% by volume;
   glycerine in an amount between about 5% and 15% by volume;
   Vitamin A in an amount between about 1% and 5% by volume;
   propylene glycol in an amount between about 20% and 40% by volume;
   an antibacterial and fungal agent in an amount which is greater than a trace amount and less than about 5% by volume;
   a buffering agent in an amount which maintains a pH of about 6.0 to 7.0; and
   an emulsifier in an amount which is greater than a trace amount and less than about 5% by volume.

10. The method of claim 9 further including the step of placing the composition of an absorbent, disposable material.

11. A single use, dispensing package for the treatment of hemorrhoidal tissue, comprising:
   a disposable, single use, nonadhesive absorbent material;
   means for sealing the absorbent material within an environment; and
   a composition absorbed in the absorbent material, the composition including:
      hydrocortisone acetate in an amount of between about 0.2% and 2.0by volume;
      pramoxine hydrogen chloride in an amount of between about 0.5% and 3.0% by volume;
      ephedrine sulfate in an amount of between about 0.1% and 1.0% by volume;
      witch hazel in an amount of between about 30% and 60% by volume;
      glycerine in an amount of between about 5% and 15% by volume;
      Vitamin A in an amount of between about 1% and 5% by volume;
      propylene glycol in an amount of between about 20% and 40% by volume;
      methylparaben in an amount of between about 0.25% and 1% by volume;
      an emulsifier in an amount of between about 0.1% and 5% by volume; and
      a buffering agent.

12. The package of claim 11 wherein the witch hazel is in an amount of about 50% by volume.

13. The package of claim 12 wherein the glycerine is in an amount of about 10% by volume.

14. The package of claim 13 wherein the Vitamin A is in an amount of about 3% by volume.

15. The package of claim 14 wherein the propylene glycol is in an amount 34% by volume.

16. The package of claim 15 wherein the methylparaben is in an amount which is about 0.5% by volume.

17. The package of claim 16 wherein the buffering agent maintains the pH of the composition at about 6.0 to 7.0.

18. The method according to claim 9 wherein the hydrocortisone compound is present in an amount which is about 0.25% by volume.

19. The method according to claim 9 wherein the pramoxine hydrogen chloride is present in an amount which is about 0.5% by volume.

20. The method according to claim 9 wherein the ephedrine sulfate is present in an amount which is about 0.1% by volume.

* * * * *